United States Patent
Jeong et al.

(10) Patent No.: US 6,656,121 B2
(45) Date of Patent: Dec. 2, 2003

(54) METHOD OF QUANTITATIVELY MEASURING FAT CONTENT IN TARGET ORGAN FROM ULTRASOUND VISUAL IMAGE

(75) Inventors: Ji-wook Jeong, Daejon (KR); Soo-yeul Lee, Daejon (KR); Seung-hwan Kim, Daejon (KR)

(73) Assignee: Electronics and Telecommunications Research Institute, Daejon (KR)

( * ) Notice: Subject to any disclaimer, the term of this patent is extended or adjusted under 35 U.S.C. 154(b) by 0 days.

(21) Appl. No.: 10/205,104

(22) Filed: Jul. 24, 2002

(65) Prior Publication Data

US 2003/0144592 A1 Jul. 31, 2003

(30) Foreign Application Priority Data

Jan. 31, 2002 (KR) .......................................... 2002-5642

(51) Int. Cl.[7] ................................................. A61B 8/00
(52) U.S. Cl. ..................... 600/443; 600/449; 600/437
(58) Field of Search ................................. 600/437, 449, 600/443, 442, 587; 382/128

(56) References Cited

U.S. PATENT DOCUMENTS 5,339,815 A * 8/1994 Liu et al. ..................... 600/437
5,398,290 A * 3/1995 Brethour ....................... 382/128
5,941,825 A * 8/1999 Lang et al. ................... 600/449

FOREIGN PATENT DOCUMENTS

KR      1999-0073283       6/1999

OTHER PUBLICATIONS

Quantitative Estimation of Attenuation in Ultrasound Video Images, pp. 319–324.

=Abstract= Differentiation of Hepatocellular Carcinoma from Hemangiona: Computer–Aided Tissue Echo Quantification, 1997; 16; pp. 209–213.

* cited by examiner

Primary Examiner—Marvin M. Lateef
Assistant Examiner—Ruby Jain
(74) Attorney, Agent, or Firm—Blakely, Sokoloff, Taylor & Zafman

(57) ABSTRACT

A method of quantitatively assessing fat content in a target organ from an ultrasound visual image is provided. This method includes obtaining an ultrasound visual image of the target organ, setting a target region in the obtained image, measuring a quantified representative gray level of the target region from a gray level distribution of pixels of the target region, and assessing fat content corresponding to the quantified representative gray level of the target region.

10 Claims, 9 Drawing Sheets

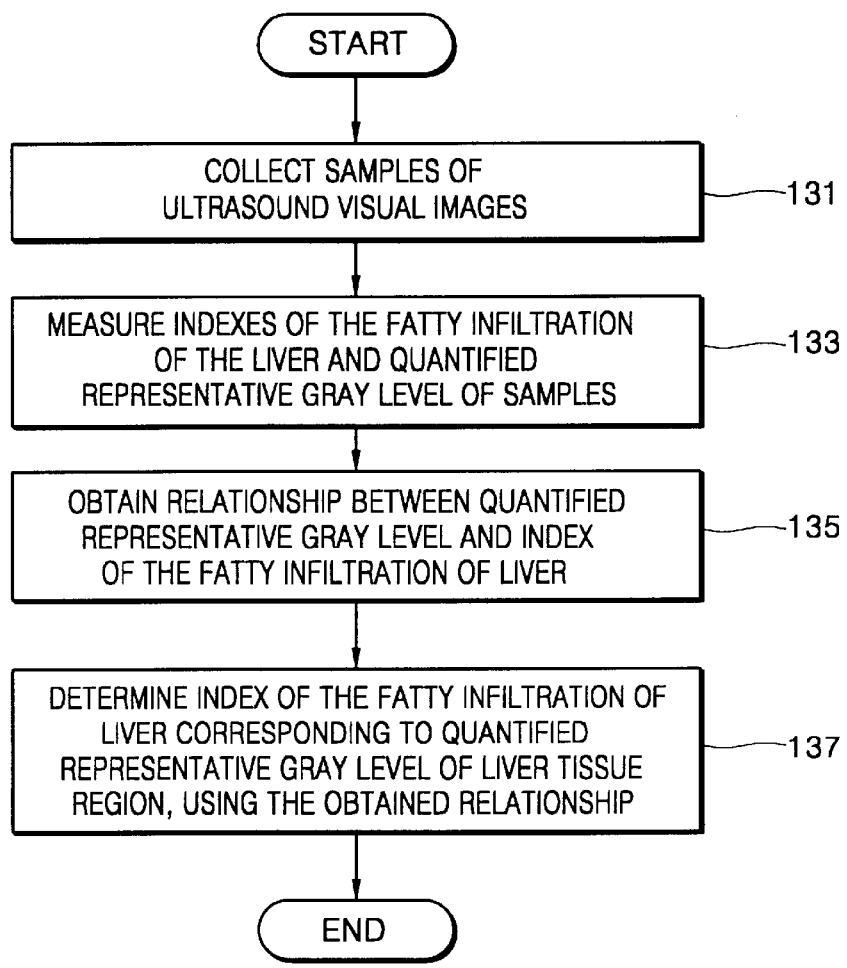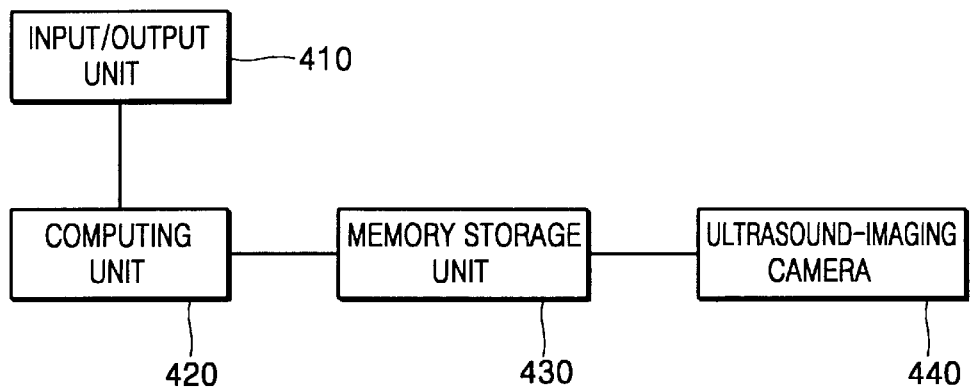

METHOD OF QUANTITATIVELY MEASURING FAT CONTENT IN TARGET ORGAN FROM ULTRASOUND VISUAL IMAGE

BACKGROUND OF THE INVENTION

1. Field of the Invention

The present invention relates to an ultrasound image of a cross-section of an organ of a human body, taken by ultrasonography, and more particularly, to a method of measuring fat content in a target organ by quantitatively assessing from the gray level distributions of pixels of an ultrasound visual image.

2. Description of the Related Art

Deposit of fat in a human organ may cause various complications, and results in the functional disorder of the organ. For instance, a fatty liver contains abnormally much fat, which, however, does not cause a pain and there is no particular subjective symptoms. Although a slight fatty liver can be found in a healthy person, there is a high probability that fat content in the liver increases abnormally and causes a complication or hepatocirrhosis. In this regard, diet life and obesity become social issues today, which draw much attention upon quantitative assessment of fat content in a human liver. As a result, methods of easily measuring fat content in a human organ at low cost have been continuously developed.

It is generally known that a fatty liver has a very close connection with fat content in a liver. Although various methods of quantitatively assessing fat content in a target organ have been continuously suggested or carried out, there is a growing need for a method of easily measuring fat content in a target organ of a human body at lower cost.

In order to assess fat content in a human organ, computed tomography (CT) is frequently used in obtaining a visual image of a cross-section of a human organ. CT is advantageous in that a visual image of high resolution can be obtained, and it is possible to precisely separate a ratio of fat content or other substances from a visual image irrespective of scanning techniques or ambient conditions. Nevertheless, it is very expensive to use CT, and further, there is much adverse criticism about the use of CT on a human body in that the human body is exposed to radioactive rays.

Meanwhile, fat content in a human organ is measured through hepatic biopsy. Hepatic biopsy is to analyze a tissue and substances of an organ taken off from a human body, e.g., a hepatic tissue, and can provide the most fundamental and exact diagnosis and inspection of hepatic disease. However, hepatic biopsy is very difficult to carry out and dangerous in terms of the invasiveness. Further, there is a strong tendency that hepatic biopsy is used when a patient does feel particular symptoms of disease. Therefore, in fact, hepatic biopsy is almost useless for preventive treatment.

On the other hand, ultrasonography is of wide use because it is possible to easily and cheaply obtain a visual image of a cross-section of a human body, including a cross-section of a belly, and diagnose and inspect the state of the human organ from the obtained visual image. Especially, ultrasonography is safe in that it does not use radioactive rays, and is not invasive. Despite these advantages, the quality of an ultrasound visual image is dependent greatly upon scanning techniques and ambient conditions, and the reflective characteristics and resolution of an object through which ultrasound wave passes are irregular. For these reasons, there is a higher probability that a person who diagnoses patient's disease may put an arbitrary interpretation on a visual image taken by ultrasonography, thereby lowering the reliability of his/her diagnosis.

At the present time, the clinical determination of a fatty liver is largely divided into four levels, using ultrasonography: normal, mild, moderate, severe. However, an error range of the level of a fatty liver diagnosed by therapists who have experienced to diagnose patents' diseases using ultrasonography, is within one level, and the probability that an error occurs is 20% at maximum.

Accordingly, there is a growing need for a method of quantitatively measuring fat content in a target organ, which uses ultrasonography that is simple and inexpensive to use, but is not affected by scanning techniques or ambient conditions. Although there are many methods of measuring fat content in a human organ only with ultrasonography, it is difficult to quantitatively measure fat content in an organ due to the distortion of image characteristics caused by an irregular gray level distribution and poor resolution of an ultrasound visual image. Also, the reliability of the result according to these methods is low.

SUMMARY OF THE INVENTION

To solve the above-described problems, it is an object of the present invention to provide a method of quantitatively assessing fat content in a target organ by measuring the gray level distribution of the target organ from an visual image taken by ultrasonography, and extracting a representative gray level.

Accordingly, to achieve an aspect of the above object, there is provided a method of quantitatively assessing fat content in a target organ from an ultrasound visual image, the method including obtaining an ultrasound visual image of the target organ, setting a target region in the obtained image, measuring a quantified representative gray level of the target region from a gray level distribution of pixels of the target region, and assessing fat content corresponding to the quantified representative gray level of the target region.

Here, the ultrasound visual image may be an image of a cross-section of a human belly, and the target region may include a human liver.

Measuring the representative gray level of the target region may include obtaining a distribution pattern of pixels of the target region, obtaining histogram distributions of the number of pixels with regard to gray levels of pixels of the target region, and determining the gray level of one histogram of the histogram distributions as the representative gray level. The representative gray level of the target region may be determined as a gray level of a histogram positioning at a point of inflection in the histogram distribution.

To achieve another aspect of the above object, there is provided a method of quantitatively assessing fat content in a target organ from an ultrasound visual image, the method including obtaining an ultrasound visual image of the target organ, setting a target region and comparative regions in the obtained image, measuring a representative gray level of the target region from a gray level distribution of pixels of the target region, measuring representative gray levels of the comparative regions from the gray level distributions of pixels of the comparative regions, quantifying the representative gray level of the target region as relative values as compared with the representative gray levels of the comparative regions, and assessing fat content corresponding to the quantified representative gray level of the target region.

Measuring the representative gray levels of the comparative region may include setting a path across each comparative region, obtaining a pixel distribution pattern of gray levels along the path, obtaining a distribution graph of gray levels of pixels along the path, and calculating an average of gray levels corresponding to maximum points in the distribution graph of the gray levels, and determining the average as the representative gray level of the comparative region.

Otherwise, measuring the representative gray level of the comparative region may include setting a path across each comparative region, obtaining a pixel distribution pattern of gray levels along the path, obtaining a distribution graph of gray levels of the pixels along the path, and calculating an average of gray levels corresponding to minimum points in the distribution graph of the gray levels, and determining the average as the representative gray level of the comparative region.

Otherwise, measuring the representative gray level of the comparative region may include setting a path across the comparative region, obtaining a pixel distribution pattern along the path, obtaining a histogram distribution of the number of pixels with regard to gray levels of the pixels, and calculating an average of some gray levels from the histogram distributions, and determining the average as the representative gray level of the comparative region.

Assessing fat content in the target organ may include collecting samples of ultrasound visual images, measuring quantified representative gray levels of the samples, and actual fat contents, obtaining a proportional function with regard to the quantified representative gray levels of the samples and the actual fat contents, and assessing fat content corresponding to the quantified representative gray level of the target region, using the proportional function.

According to the present invention, fat content in a human organ can be effectively and reliably measured from an ultrasound visual image thereof at low cost. A method of quantitatively assessing fat content in a human organ from an ultrasound visual image, according to the present invention, is very effective and reliable. Further, this method provides safe quantitative assessment of fat content at low cost.

BRIEF DESCRIPTION OF THE DRAWINGS

The above objects and advantages of the present invention will become more apparent by describing in detail a preferred embodiment thereof with reference to the attached drawings in which:

FIG. 3 is a flow chart explaining a method, according to the present invention, of determining actual fat content from a quantified representative grays level;

FIG. 4 is a schematic block diagram of an apparatus, according to the present invention, used in quantitatively measuring fat content in a target organ from an ultrasound visual image;

DETAILED DESCRIPTION OF THE INVENTION

Figure 1:
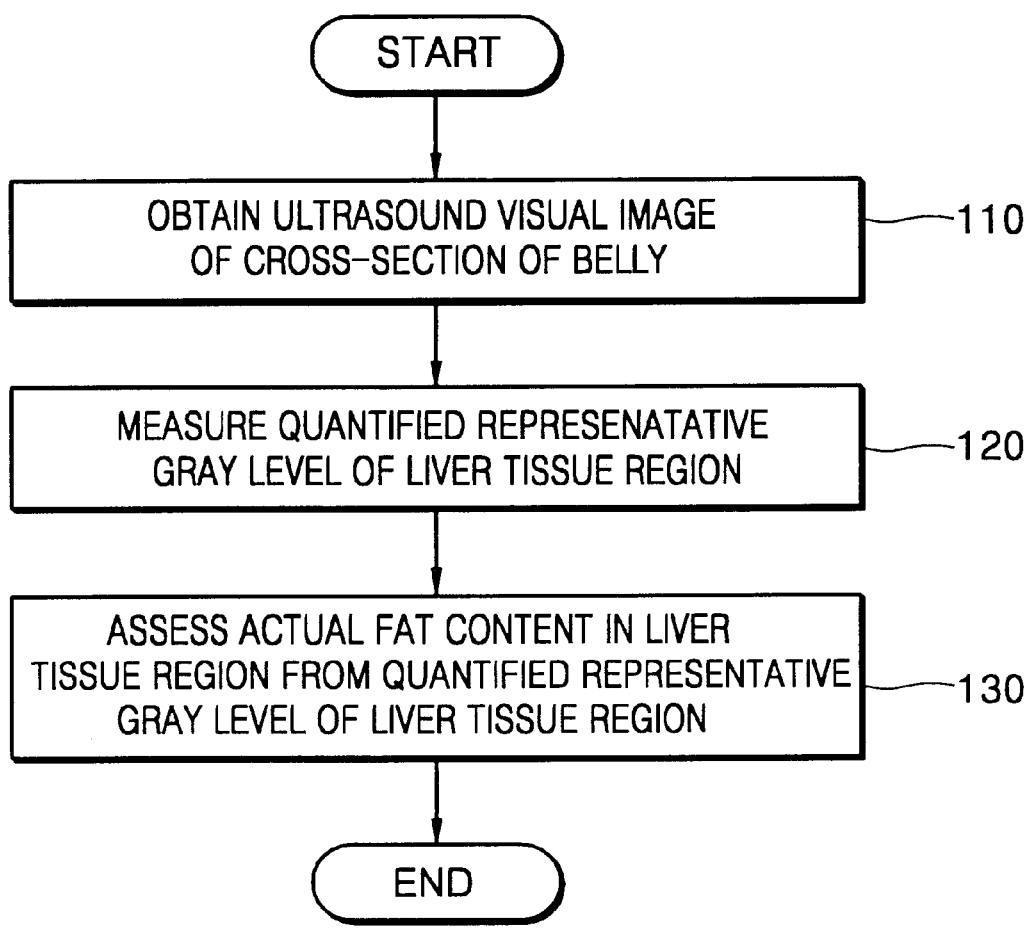
FIG. 1 is a flow chart explaining a method of quantitatively measuring fat content in a target organ from an ultrasound visual image according to the present invention.

The present invention now will be described more fully with reference to the accompanying drawings, in which a preferred embodiment of the invention is shown. This invention may, however, be embodied in many different forms and should not be construed as being limited to the embodiment set forth herein; rather, this embodiment is provided so that this disclosure will be thorough and complete, and will fully convey the concept of the invention to those skilled in the art. In the drawings, the shape or size of elements is exaggerated for clarity, and the same reference numerals in different drawings represent the same element, and thus their description will be omitted.

A preferred embodiment of the present invention to be described below provides a method of indexing variations in the reflective and refractive characteristics of a human organ under fatty degeration, i.e., a target organ, with regard to ultrasound waves, using an ultrasound visual image, and estimating the degree of fat content in the target organ from obtained indexes.

Here, an ultrasound visual image, such as an image of a cross-section of a human belly taken by ultrasonography, is an image made by converting the reflective and refractive characteristics of a corresponding organic tissue with regard to ultrasound waves into a gray level, and then recomposing the gray level into a two-dimensional image. In general, the main elements constituting an organic tissue are fat and water. When ultrasound waves pass the organic tissue, fat and water have different reflective characteristics from each other. For instance, in an ultrasound visual image, a fat region appears brighter than a water region. Therefore, the gray level or brightness of a pixel in a cross-sectional image of a human belly, taken by ultrasonography, increase in proportion to fat content in an organic tissue corresponding to the pixel.

However, the gray level or brightness of a pixel does not represent the fat content in the target organ directly. This is because the gray level of a pixel may vary according to ambient conditions and scanning techniques when a cross-sectional image of a human belly is taken by ultrasonography. Therefore, the gray level of a pixel cannot be used as indexes of fat content in an organ. For example, when an object is taken by ultrasonography two times at the same position of an organ under different ambient conditions, the two gray levels of the pixels obtained from two images at the same position may not be the same. For this reason, the gray level of an ultrasound visual image cannot be a factor that determines fat content in an organ.

To solve this problem, in this embodiment of the present invention, a method of obtaining and quantifying a representative gray level of a corresponding region of an organ, i.e., a target region, and estimating fat content in the target region. That is, this method allows the use of the representative gray level as an index value indicating fat content in the target organ, irrespective of conditions under which an ultrasound visual image of a cross-section of the target organ is obtained in order to quantify representative gray level, for example, ambient conditions.

Referring to FIG. 1, a method of quantitatively measuring fat content in a target organ, according to the present invention, includes obtaining an ultrasound visual image of a cross-section of a belly, in step 110, measuring a quantified representative gray level of a target organ, e.g., a liver region in step 120, and measuring actual fat content in the liver region from the obtained representative gray level, in step 130. FIG. 1 is a flow chart explaining a method of quantitatively measuring fat content in a target organ, according to a preferred embodiment of the present invention, from an ultrasound visual image.

Figure 5:
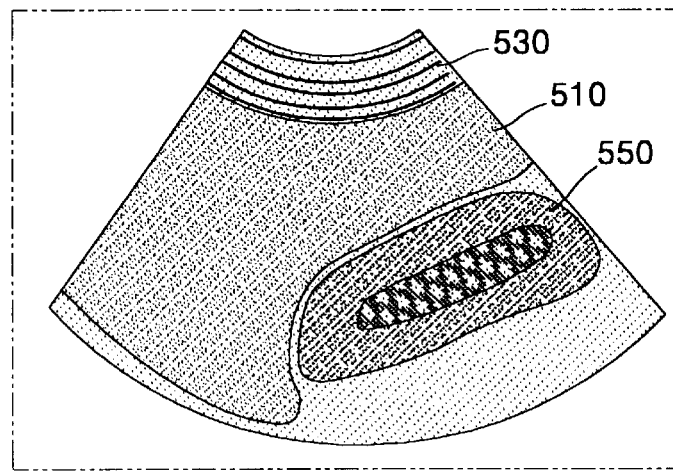
FIG. 5 is a schematic view of an example of an image taken by ultrasonography.

An ultrasound visual image of a cross-section of a belly as shown in FIG. 5 is obtained by taking an ultrasound visual image of a human belly by ultrasonography. At this time, preferably, a scanning angle and the degree of contact are adjusted to make the distribution of gray levels of the ultrasound visual image as clear as possible. Also, preferably, the obtained ultrasound visual image includes cross-sections of all organs such as a liver region, a kidney, and a subcutaneous fat region of a belly.

At this time, the ultrasound visual image is taken by an ultrasound-imaging facility 440 included in an apparatus, as shown in FIG. 4, that is used for quantitatively measuring fat content in a target organ from an ultrasound visual image. FIG. 4 is a schematic block diagram of an apparatus for quantitatively measuring fat content in a target organ from an ultrasound visual image. The ultrasound-imaging facility 440 may be a typical ultrasound-imaging facility. Image data taken by the ultrasound-imaging facility 440 is stored as digital data in a memory storage unit 430. Data stored in the memory storage unit 430 is used to measure, determine and quantify a representative gray level by a computing unit 420, and estimate fat content of a target organ from the representative gray level under the control of an input/output unit 410.

The obtained ultrasound visual image of a cross-section of a belly consists of pixels of gray levels from 0 to 255. Here, the typical number of pixels may be set by 500×700. Data regarding the ultrasound visual image is processed by the computing unit 420, and output to a monitor of the input/output unit 410.

Figure 2:
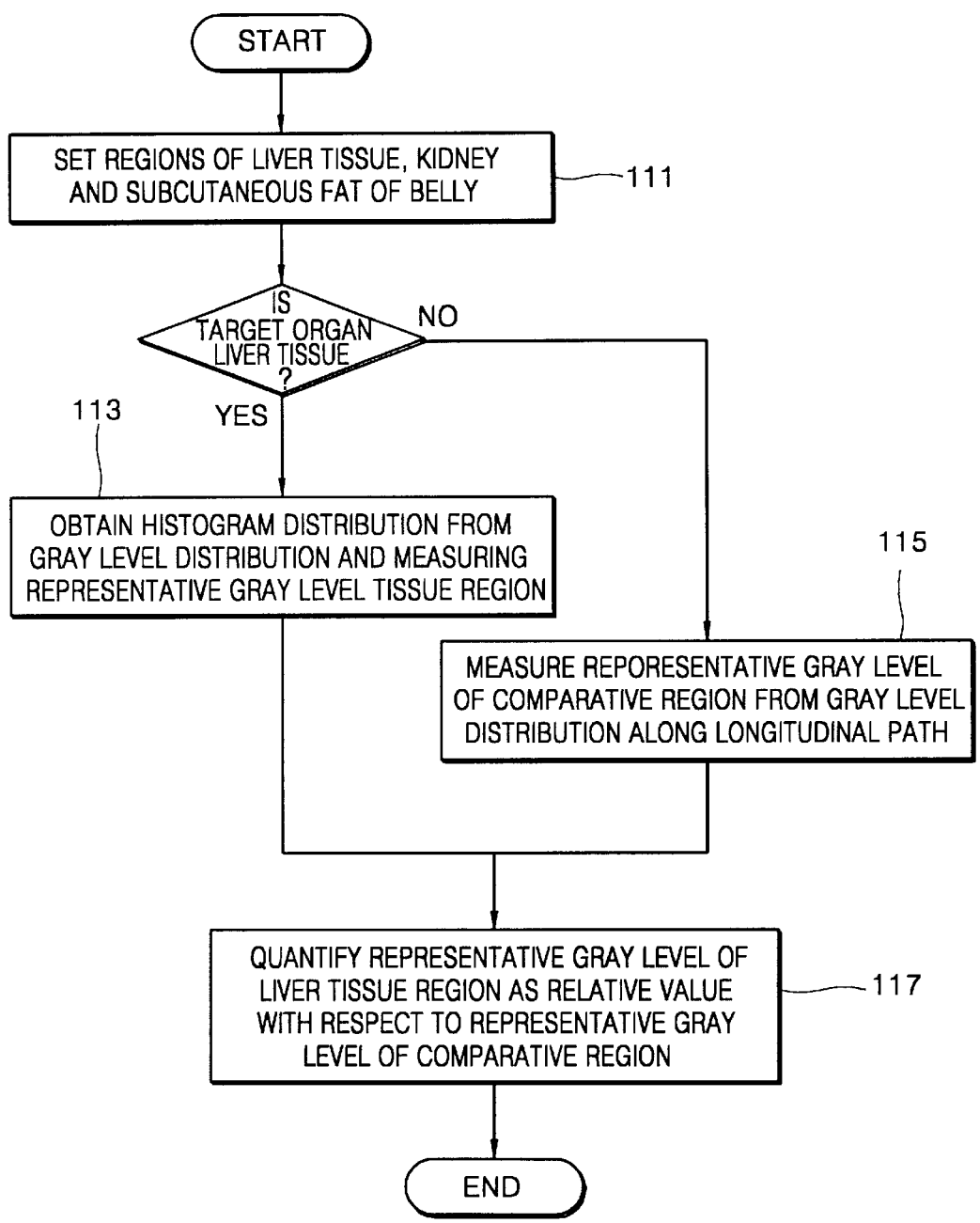
FIG. 2 is a flow chart explaining a method of obtaining quantified representative gray level of an ultrasound visual image according to the present invention.

To extract a representative gray level of a target organ, i.e., a liver region, from the ultrasound visual image of a cross-section of the belly, a target region is set in the ultrasound visual image. FIG. 2 is a flow chart explaining a method of extracting the quantified representative gray level from an ultrasound visual image, according to a preferred embodiment of the present invention. In detail, as shown in FIG. 5, a liver region is set to be a target region 510 in the ultrasound visual image of a cross-section of a human belly. Then, comparative regions 530 and 550 are set to quantify a representative gray level with regard to the target region 510, in step 111.

As a comparative value used to quantify the liver region, which is the target region 510, an organ having the maximum or minimum fat content in a human body may be selected. In this embodiment, a subcutaneous fat region of a belly, which has the maximum fat content, is selected as the first comparative region 530, and a kidney, especially adrenal cortex having the minimum fat content is selected as the second comparative region 550.

First, in case that the regions to be measured are the comparative regions 530 and 550 other than a liver region, representative gray levels are extracted from the comparative regions 530 and 550, so that the representative gray levels are used to quantify a representative gray level to be extracted from the target region 510 that is the liver, in step 115. The representative gray levels of the comparative regions 530 and 550 are determined after obtaining the gray level distribution of pixels of the comparative regions 530 and 550.

Figure 7:
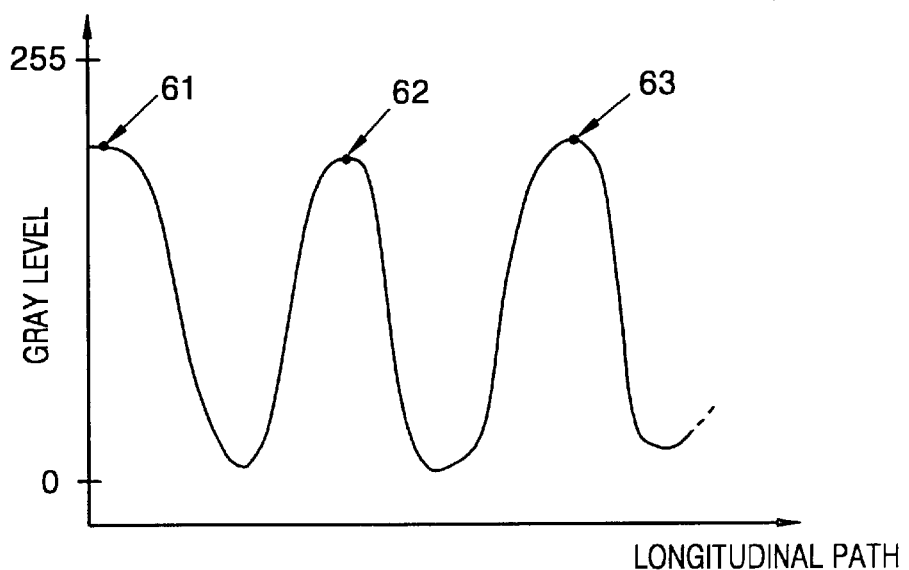
FIG. 7 is a graph illustrating variations in the grays level distribution in the longitudinal path of the first comparative region of FIG. 6.

More specifically, the first comparative region 530, which is a subcutaneous fat region of a human belly, is typically illustrated as shown in FIG. 5. After setting a longitudinal path in the first comparative region 530, the distribution of gray levels, which are extracted from the longitudinal path, can be illustrated as a graph as shown in FIG. 7. Referring to FIG. 7, gray levels corresponding to the maximum points 61, 62 and 63 of the distribution graph along the longitudinal path are extracted, and an average value of these points may be calculated as a representative gray level of the first comparative region 530.

Preferably, maximum gray levels are extracted as comparative values useful in quantifying a representative gray level of a target organ because the subcutaneous fat of the belly contains much fat content. In general, a fat region appears bright, that is, it gives a high gray level in an ultrasound visual image. Here, the setting of or arithmetic operations required for extracting gray levels of the regions are carried out by the computing unit 420 such as a micro processor.

Here, the representative gray level of the first comparative region 530, which is a subcutaneous fat region of a belly, may be determined to be about 228.9 by the above method.

Figure 6:
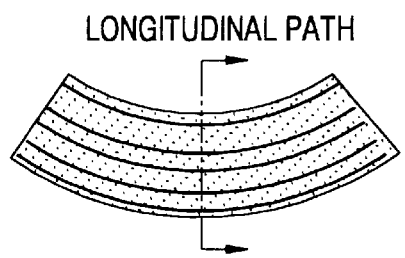
FIG. 6 is a schematic view of a first comparative region that is a subcutaneous fat region in a belly.
Figure 8:
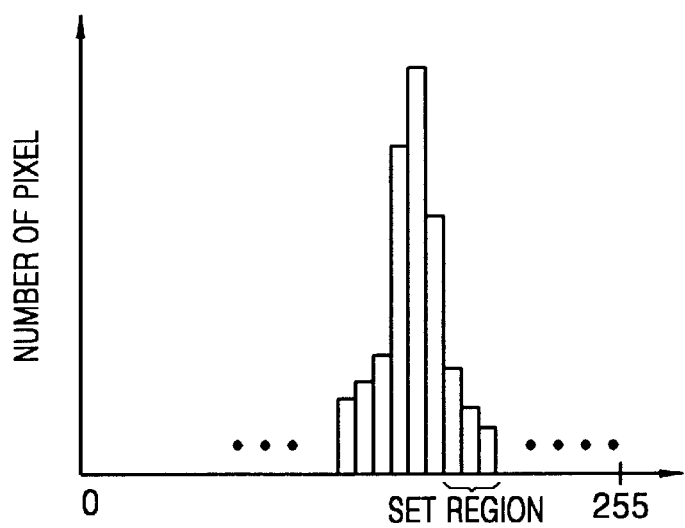
FIG. 8 is a histogram distribution illustrating the rough distribution of the number of pixels with regard to the gray levels on the longitudinal path in the first comparative region of FIG. 6.

Meanwhile, the representative gray level of the first comparative region 530 may be extracted from a histogram distribution of gray levels on the longitudinal path of FIG. 6. FIG. 8 is a histogram distribution of the number of pixels with regard to gray levels on the longitudinal path. At this time, since the subcutaneous fat region of a belly contains considerably much fat content, corresponding to higher gray levels in the histogram distribution, and an average value of these gray levels may be calculated as a representative gray level of the first comparative region 530.

Figure 9:
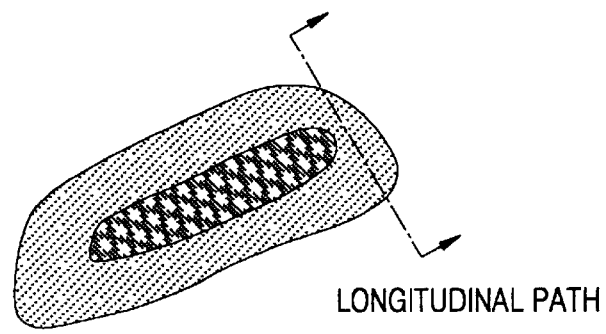
FIG. 9 is a schematic view of a second comparative region that is a kidney region.

As described above, the subcutaneous fat region of a belly, which contains more fat content, is determined as the first comparative region 530, and a representative gray level of the first comparative region 530 is calculated. Then, a kidney ,especially adrenal cortex, which contains less fat content, is set as the second comparative region 550. FIG. 9 is a view of the second comparative region that is a kidney. After setting a longitudinal path on the second comparative region 550 of FIG. 5, the distribution of gray levels on the longitudinal path is illustrated as a graph as shown in FIG.

Figure 10:
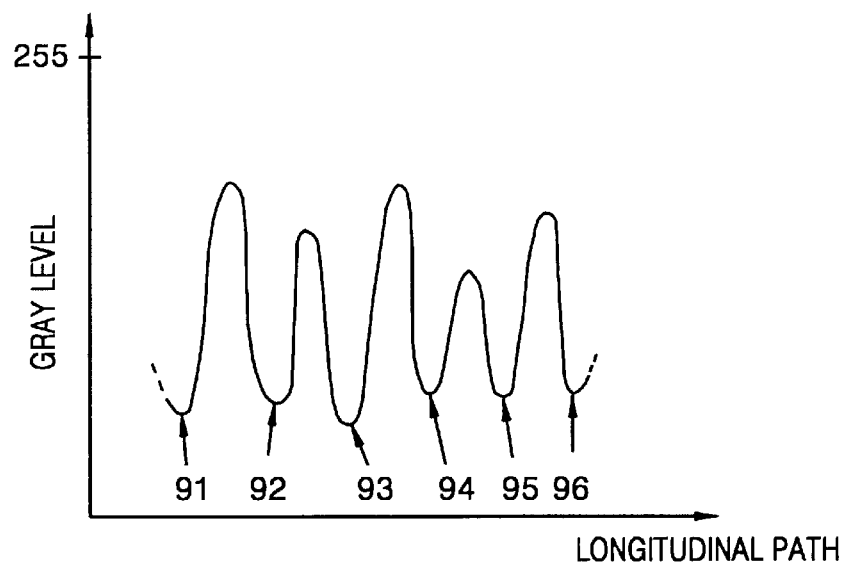
FIG. 10 is a graph illustrating variations in the gray level distribution on the longitudinal path of the second comparative region of FIG. 9.

10. Referring to FIG. 10, gray levels corresponding to minimum points 91 through 96 are extracted, and an average of these gray levels may be calculated as a representative gray level of the second comparative region 550 that is a kidney.

Kidney, especially adrenal cortex is a region of less fat content, and therefore, preferably, low gray levels are extracted as comparative values in order to quantify a representative gray level of a target region. Setting or an operation on the comparative values may be performed by the computing unit 420 such as a microprocessor, as shown in FIG. 4.

Here, the representative gray level of the second comparative region 550, which is a kidney region, especially adrenal cortex, may be determined to be about 47.7 by the above extraction method.

Figure 11:
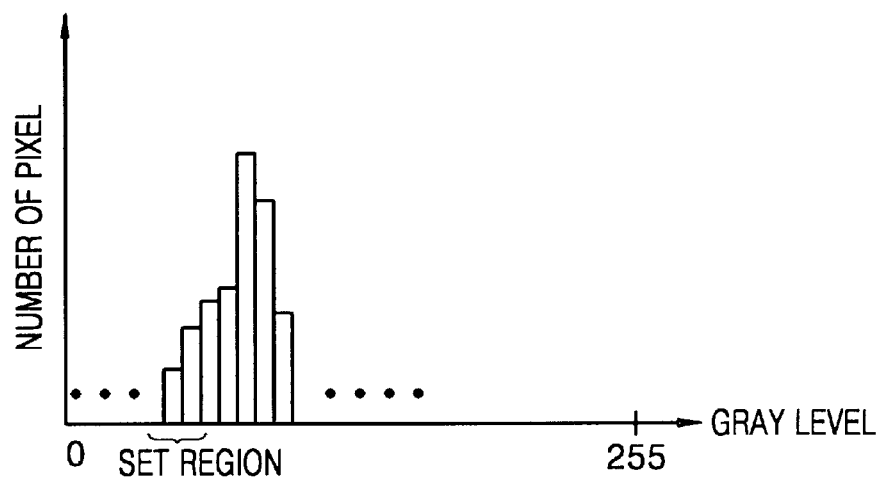
FIG. 11 is a histogram distribution illustrating the distribution of the number of pixels with regard to the gray levels on the longitudinal path of the second comparative region of FIG. 9.

Meanwhile, the representative gray level of the second comparative region 550 may be extracted from a histogram distribution of gray levels on the longitudinal path of FIG. 9. FIG. 11 is a histogram distribution of the number of pixels with regard to gray levels on the longitudinal path of FIG. 9. Since a kidney region, especially adrenal cortex has very low fat content, low gray level regions are determined in the histogram distribution, and an average value of their gray levels is calculated as the representative gray level of the second comparative region 550.

Once the representative gray levels of the comparative regions 530 and 550, which are to be used as comparative values with regard to the representative gray level of the target region 510, are determined, the representative gray level of the target region 510 is obtained, in step 113 of FIG. 2.

Figure 12:
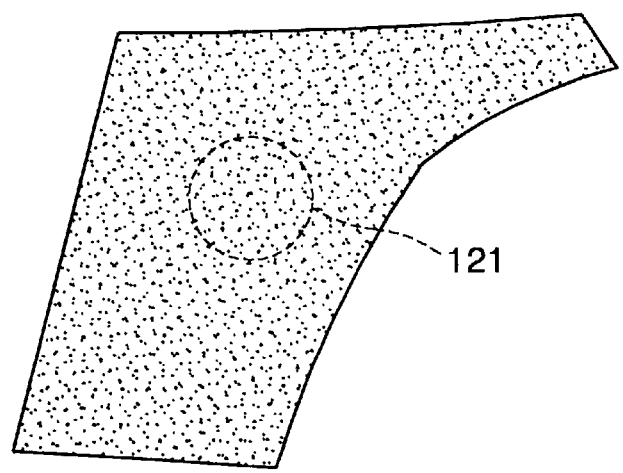
FIG. 12 is a schematic view of a liver region.

More specifically, it is known that fat is relatively homogeneously distributed throughout a liver region, which is the target region 510 shown in FIG. 12, a portion of the target region 510 is determined as a set region 121, gray levels of pixels in the set region 121 are analyzed, and the representative gray level is obtained. FIG. 12 is a view of a typical liver region that is the target region 510.

Figure 13:
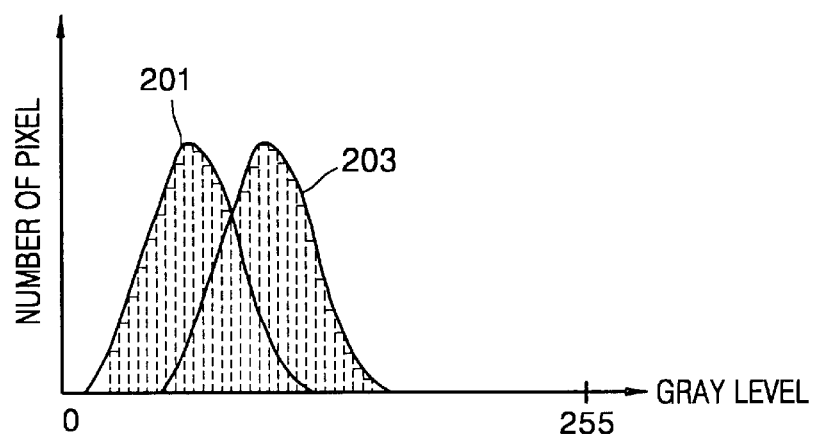
FIG. 13 is a histogram distribution illustrating the rough distribution of the number of pixels with regard to the gray levels in the region of FIG. 12.

A histogram distribution of the number of pixels with regard to the gray level of each pixel is obtained by analyzing the gray levels of the pixels in the set region 121 in the target region 510, and then, the representative gray level is extracted from the histogram distribution in step 113 of FIG. 12. For instance, referring to FIG. 13, a histogram distribution of the number of pixels with regard to gray levels is obtained and noise is filtered based on the obtained histogram distribution. Here, Gaussian broadening is used to reduce noise. FIG. 13 shows a rough histogram distribution of the target region 510.

Figure 14:
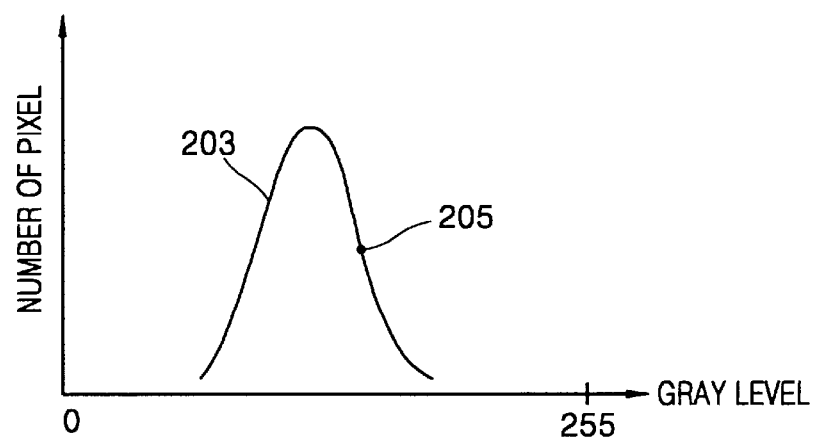
FIG. 14 is a histogram distribution graph that is filtered and separated from the histogram distribution of FIG. 13.

The histogram distribution can be filtered into two distribution graphs 201 and 203, as shown in FIG. 13. Here, the distribution graph 203, which represents a brighter gray level region having much fat content, is separately indicated in FIG. 14. A first point of inflection 205 on a bright side of the histogram distribution graph 203 is selected, and its gray level is determined as a representative gray level. In this case, the representative gray level of the target region 510, which is a liver region, may be extracted as 198.6, for example.

Referring to FIG. 2, after extracting the representative gray level of the target region 510 in step 113 or 115, the obtained representative gray level is quantified, in step 117. This quantification may be made by quantifying the representative gray level of the target region 510 as a relative value compared to certain regions, other than the target region 510 of an ultrasound visual image of a belly including the target region 510. For instance, the representative gray level of the target region 510 is quantified or standardized as a relative value with regard to the representative gray levels of the first comparative region 530, which is a subcutaneous region of a belly having the maximum fat content, and the second comparative region 550 which is a kidney, especially adrenal cortex region of the minimum fat content.

If the quantified representative gray level of the target region 510, the representative gray level of the target region 510, the representative gray level of the first comparative region 530, and the representative gray level of the second comparative region 550 are set as C', C, A, and B, respectively, C' can be calculated with a function, f(C; A,B) and quantified. Also, in case that f(C; A,B) is equivalent to (C-B)/(A-B), C', which is the quantified representative gray level of the target region 510, can be calculated as a quantified value. Here, the function, f(C; A,B) may be any function that monotonically increases.

The representative gray level of the target region 510, which is calculated with the above function and quantified, is obtained as (198.6−47.7)/(228.9−47.7)=0.833. The quantified representative gray level of the target region 510 is quantified as a relative value with regard to those of comparative regions, within a range from 0 to 1. Therefore, this representative gray level can be compared with a the quantified representative value obtained from another ultrasound visual image.

Referring to FIG. 1, actual fat content is obtained from the quantified representative gray level of the target region 510, in step 130. FIG. 3 is a flow chart briefly explaining a method of calculating actual fat content from a quantified representative gray level of the target region 510. More specifically, first, a functional relationship between the quantified representative gray level of the target region 510 and fat content in the actual target region 510 is obtained. To obtain the above functional relationship, ultrasound visual images of a cross-section of a target region is collected, in step 131. Next, for a target region of each sample indexes of the fatty infiltration of liver and quantified representative gray level of a liver are obtained, in step 133. The quantified representative gray levels are obtained by the above method.

Figure 15:
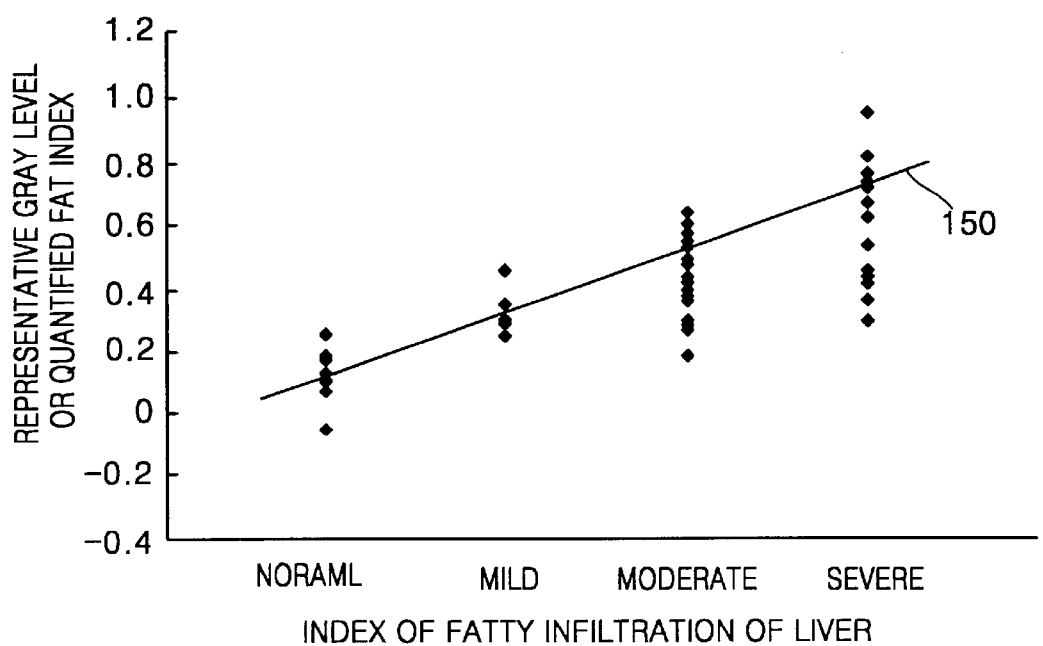
FIG. 15 is a graph illustrating the relationship between the index of a fatty liver and a quantified representative gray levels.

Then, a correlation between the quantified representative gray levels and indexes of the fatty infiltration of liver is obtained, in step 135. For instance, as shown in FIG. 15, a distributional diagram of quantified representative gray levels of the indexes of the fatty infiltration of liver obtained. FIG. 15 is a graph illustrating the relationship between indexes of the fatty infiltration of liver and a quantified representative gray level. Here, indexes of the fatty infiltration of liver are those obtained actually by clinician. Then, a proportional function between indexes of the fatty infiltration of liver and quantified representative gray levels is calculated by a least-square method. Such a proportional function can be expressed as a proportionally increasing line 150 in FIG. 15.

A corresponding indexes of the fatty infiltration of liver is obtained by applying the quantified gray level of the target region 510 to a correlation function, in step 137. Thus, the quantified representative gray level obtained from this embodiment can be estimated or regarded as a corresponding indexes of the fatty infiltration of liver.

As described above, according to the present invention, a representative gray level of a desired region of a target organ can be assessed by linearly adjusting gray level distribution of pixels of ultrasound visual images, irrespective of scanning techniques or ambient conditions. Also, quantification of the obtained representative gray level allows ultrasound visual images to be compared with one another and its fat content of the target organ to be quantitatively measured.

What is claimed is:

1. A method of quantitatively assessing fat content in a target organ from an ultrasound visual image, the method comprising:

obtaining an ultrasound visual image of the target organ;

setting a target region and comparative regions in the obtained image;

measuring a representative gray level of the target region from a gray level distribution of pixels of the target region;

measuring representative gray levels of the comparative regions from the gray level distribution of pixels of the comparative regions;

quantifying the representative gray level of the target region as relative values with regard to the representative gray levels of the comparative regions; and assessing fat content corresponding to the quantified representative gray level of the target region, wherein said target region measuring includes:

obtaining a distribution pattern of pixels of the target region;

obtaining histogram distributions of the number of pixels with regard to gray levels of each pixel of the target region; and determining the gray level of one histogram of the histogram distributions as the representative gray level, and wherein the representative gray level of the target region is determined as a gray level of a histogram positioning at a point of inflection in the histogram distribution.

2. The method of claim 1, wherein the ultrasound visual image is an image of a cross-section of a human belly.

3. The method of claim 1, wherein the target region comprises a human liver.

4. The method of claim 1, wherein the comparative regions comprise a subcutaneous fat region of a belly and a kidney.

5. The method of claim 1, wherein the point of inflection is a first point of inflection of a brighter side than the maximum of the number of the pixel in the histogram distribution.

6. The method of claim 1 wherein before determining the gray level of the histogram, noise is reduced from a histogram distribution that is separated from the histogram distributions by filtering and extracting a distribution graph including the maximum value of the brighter side from the histogram distributions, using Gaussian broadening.

7. The method of claim 1, wherein measuring the representative gray levels of the comparative region comprises:

setting a path across the comparative region;

obtaining a distribution pattern of pixels of the path;

obtaining distribution graphs of gray levels of pixels along the path; and calculating an average of gray levels corresponding to maximum points in the distribution graphs of the gray levels, and determining the average as the representative gray level of the comparative region.

8. The method of claim 1, wherein measuring the representative gray level of the comparative region comprises:

setting a path across each comparative region;

obtaining a pixel distribution pattern along the path;

obtaining a distribution graph of gray levels of the pixel along the path; and calculating an average of gray levels corresponding to minimum points in the distribution graph of the gray levels, and determining the average as the representative gray level of the comparative region.

9. The method of claim 1, wherein measuring the representative gray level of the comparative region comprises:

setting a path across the comparative region;

obtaining a pixel distribution pattern along the path;

obtaining a histogram distribution of the number of pixels with regard to gray levels of the pixels; and calculating an average of some gray levels from the histogram distributions, and determining the average as the representative gray level of the comparative region.

10. The method of claim 1, wherein assessing fat content in the target organ comprises:

collecting samples of ultrasound visual images;

measuring quantified representative gray levels of the samples, and actual fat contents;

obtaining a proportional function with regard to the quantified representative gray levels of the samples and the actual fat contents; and assessing fat content corresponding to the quantified representative gray level of the target region, using the proportional function.

* * * * *